(12) United States Patent
Taylor et al.

(10) Patent No.: US 7,749,708 B2
(45) Date of Patent: *Jul. 6, 2010

(54) METHOD FOR IDENTIFYING THE SEQUENCE OF ONE OR MORE VARIANT NUCLEOTIDES IN A NUCLEIC ACID MOLECULE

(75) Inventors: Paul D. Taylor, Gilroy, CA (US); Gary F. Gerard, Frederick, MD (US); Reyes Candau, Olney, MD (US)

(73) Assignee: Transgenomic, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/854,181

(22) Filed: Sep. 12, 2007

(65) Prior Publication Data

US 2009/0068652 A1    Mar. 12, 2009

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6; 536/23.1, 24.3
See application file for complete search history.

(56) References Cited

U.S. PATENT DOCUMENTS

| | | | | |
|---|---|---|---|---|
| 5,792,607 | A * | 8/1998 | Backman et al. | 435/6 |
| 5,830,721 | A * | 11/1998 | Stemmer et al. | 506/10 |
| 5,851,770 | A | 12/1998 | Babon et al. | |
| 5,869,245 | A * | 2/1999 | Yeung | 435/6 |
| 6,461,814 | B1 * | 10/2002 | Spinella | 435/6 |
| 2002/0061532 | A1 * | 5/2002 | Adams et al. | 435/6 |
| 2003/0022215 | A1 | 1/2003 | Makrigiorgos | |
| 2003/0232333 | A1 * | 12/2003 | Ladner et al. | 435/6 |
| 2004/0038258 | A1 * | 2/2004 | Harley et al. | 435/6 |
| 2004/0166510 | A1 * | 8/2004 | Gerard et al. | 435/6 |
| 2005/0089910 | A1 * | 4/2005 | Hong et al. | 435/6 |
| 2006/0024681 | A1 * | 2/2006 | Smith et al. | 435/6 |
| 2007/0128624 | A1 * | 6/2007 | Gormley et al. | 435/6 |
| 2007/0202521 | A1 * | 8/2007 | Sun | 435/6 |
| 2008/0194416 | A1 * | 8/2008 | Chen | 506/9 |

FOREIGN PATENT DOCUMENTS

| | | | |
|---|---|---|---|
| WO | 02086169 | A1 | 10/2002 |
| WO | WO 2006/053259 | A2 * | 5/2006 |

OTHER PUBLICATIONS

Yang et al. Purification, Cloning, and Characterization of the CEL I Nuclease Biochemistry 39 : 3533-3541 (2000).*
Greene et al., Spectrum of Chemically induced mutations from a large-scale reverse-genetics screen in *Arabidopis*. Genetics 164 : 731-740 (Jun. 2003.*
Oleykowski et al., Mutation detection using a novel plant endonuclease. Nucleic Acids Research 26(20) : 4597-4602 (1998).*
Kulinski et al., CEL I enzymatic mutation detection assay. Biotechniques 29(1) : 44, 46 and 48 (2000).*
Chang et al., Base mismatch-specific endonuclease activity in extracts from *Saccharomyces cerevisiae*. Nucleic Acids Research 19 (17) : 4761-4766 (1991).*
Till et al., Large-scale discovery of induced point mutations with high-throughput Tilling. Genome Research 13 : 524-530 (2003).*
Colbert et al., High-throughput screening for induced point mutations. Plant Physiology 126 : 480-484 (2001).*
Hsu et al., Detection of DNA point mutations with DNA mismatch repair enzymes. Carcinogenesis 15(8) : 1657-1662 (1994).*
Slade et al., A reverse genetic, nontransgenic approach to wheat crop improvement by Tilling. Nature Biotechnology 23(1) : 75-81 (Jan. 2005).*
Qiu et al., Mutation detection using Surveyor nuclease. Biotechniques 36(4) : 702-705 and 707 (2004).*
Sokurenko et al. Detection of simple mutations and polymorphisms in large genomic regions. Nucleic Acids Research 29(22) e111 (2001).*
Qiu et al. A method for clone specific confirmation using a mismatch-specific DNA endonuclease. Molecular Biotechnology 29 : 11-18 (2005).*
Ranasinghe et al., Fluorescence based strategies for genetic analysis Chemical Communications 44 : 5487-5502 (2005).*
Howell et al., iFRET : An improved fluorescence system for DNA-melting analysis. Genome Research 12 : 1401-1407 (2002).*
The Stragene Catalog p. 39 (1988).*
Margulies et al., "Genome sequencing in microfabricated high-density picolitre reactors", Nature 2005 437(15):376-380.
Rao et al., "Establishing a method to detect the DNA damage of N-ras gene", J. Sichuan Univ. (Med. Sci. Edi.) 2005 36:779-791—Abstract.
Robertson et al., "Genome-wide profiles of STAT1 DNA association using chromatin immunoprecipitation and massively parallel sequencing", Nature Methods 2007 4(8):651-657.
Takatsu et al., "FRET-based analysis of SNPs without fluorescent probes", Nucleic Acids Research 2004 32:e1156 (19):1-7.
Wu et al., :Study of rat's p53 gene damage and organ specifically induced by benzidine, J. Sichuan Univ. (Med. Sci. Edi.) 2006 37:33-34—Abstract.
Zhang et al., "Randomized Terminal Linker-dependent PCR: A Versatile and Sensitive Method for Detection of DNA Damage", Biomedical and Environmental Sciences 2002 15:203-208.

* cited by examiner

*Primary Examiner*—Ethan Whisenant
(74) *Attorney, Agent, or Firm*—Licata & Tyrrell P.C.

(57) ABSTRACT

The invention relates to methods for identifying the sequence of one or more variant nucleotides in a nucleic acid molecule. The method involves cleaving a double-stranded nucleic acid molecule containing a mismatch with a mismatch-specific endonuclease which cleaves on the 3' side of the mismatch, and preserving the integrity of the variant nucleotide by ligating a double-stranded linker with a 3'-overhang to said variant nucleotide. Because the variant nucleotide is immediately adjacent to the linker, PCR and/or sequence-by-synthesis analysis can be readily carried out.

12 Claims, 6 Drawing Sheets

SEQUENCE LISTING

```
<160> NUMBER OF SEQ ID NOS: 13

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1
tgtaaaacga cggccagt                                                 18

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t

<400> SEQUENCE: 2
nnnacatttt gctgccggtc a                                             21

<210> SEQ ID NO 3
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 3
acacctgatc aagcctgttc atttgattac                                    30

<210> SEQ ID NO 4
<211> LENGTH: 30
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Nucleotide labed with biotin

<400> SEQUENCE: 4
acacctgatc aagcctgttc atttgattac                                30

<210> SEQ ID NO 5
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 5
ccaaagaatg atctgcggag cttcc                                     25

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Nucleotide labeled with biotin

<400> SEQUENCE: 6
ccaaagaatg atctgcggag cttcc                                     25

<210> SEQ ID NO 7
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 7
cgactggagc acgaggacac tactggccga cgttttacac c                   41

<210> SEQ ID NO 8
<211> LENGTH: 44
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (42)..(44)
<223> OTHER INFORMATION: n is a, c, g, or t

<400> SEQUENCE: 8
ggtgtaaaac gacggccagt agtgtcctcg tgctccagtc gnnn                44

<210> SEQ ID NO 9
<211> LENGTH: 43
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (42)..(43)
<223> OTHER INFORMATION: n is a, c, g, or t
```

-continued

```
<400> SEQUENCE: 9
ggtgtaaaac gacggccagt agtgtcctcg tgctccagtc gnn                    43

<210> SEQ ID NO 10
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: n is a, c, g, or t

<400> SEQUENCE: 10
ggtgtaaaac gacggccagt agtgtcctcg tgctccagtc gn                     42

<210> SEQ ID NO 11
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 11
ggtgtaaaac gacggccagt agtgtcctcg tg                                32

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
ccatggtaag gatatgcact c                                            21

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 13
gagtttcgcc agattcaaca tc                                           22
```

METHOD FOR IDENTIFYING THE SEQUENCE OF ONE OR MORE VARIANT NUCLEOTIDES IN A NUCLEIC ACID MOLECULE

BACKGROUND OF THE INVENTION

Identifying genome sequence variations between individuals is valued because it has the potential to explain phenotypes, disease predisposition, response to disease treatments and mechanisms of disease which may lead to more effective drug development. Sequencing the whole genomes of individuals is still an expensive and time consuming procedure although recent technologies based on sequencing-by-synthesis have made great progress. More economical, efficient and error-free methods of identifying sequence variation are needed.

The activity of mismatch-specific endonucleases has found utility in detection of sequence variations in otherwise identical DNA strands. A heteroduplex must first be produced between one reference DNA strand and the reverse complement of the sample strand. If the sequences are exactly complementary with no mismatched bases, no cleavage takes place. If, however, they are not exactly complementary and mismatched bases are present, cleavage takes place with high specificity to the sites of mismatch. The cleaved products are conventionally detected by separation technologies based on fragment size. Thus, not only is the presence of mismatches revealed, the approximate location of the mismatch can also be inferred. For final identification of the exact nature of the difference between the sequences, Sanger sequencing is conventionally employed. Mismatch-specific endonuclease activity can therefore be used in an effective screening method capable of discriminating between samples which do and do not require additional sequence analysis. Such a screening process can reduce the numbers of samples that need to be fully sequenced saving both time and money.

CEL I and CEL II DNA endonucleases are examples of endonucleases which are known to cut double-stranded DNA in both strands at sites of single-base substitution, insertion or deletion. These enzymes cleave DNA on the 3'-side of the mismatch site, generating single-stranded 3'-overhangs of one or more nucleotides (Oleykowski, et al. (1998) *Nucl. Acids Res.* 26:4597-4602; Yang, et al. (2000) *Biochemistry* 39:3533-3541; Sokurenko, et al. (2001) *Nucl. Acids Res.* 29:e111; Qiu, et al. (2004) *BioTechniques* 37:702-707). These enzymes are routinely used to detect and map the location of unknown mutations in PCR-amplified DNA fragments (see, e.g., Kuliski, et al. (2000) *BioTechniques* 29:44-48; Colbert, et al. (2001) *Plant Physiol.* 126:480-484; Till, et al. (2003) *Genome Res.* 13:524-530; Greene, et al. (2003) *Genetics* 164:731-740; Slade, et al. (2005) *Nat. Biotechniques* 23:75-81). Detection and mapping involves PCR amplification of target DNA, annealing of the amplified DNA to form a mixture of homoduplices and heteroduplices, digestion with mismatch-specific endonuclease, and fractionation of the undigested homoduplices and heteroduplices from the digested products on a platform that separates DNA fragments based upon size. Endonuclease mutation detection and mapping, however, does not reveal the identity of a mutation, which requires DNA sequencing. Therefore, there is a need in the art to simplify mutation detection and concurrently determine the nature of the variation. The present invention meets this need in the art.

SUMMARY OF THE INVENTION

The present invention is a method for identifying the sequence of one or more variant nucleotides in a nucleic acid molecule. The method of the invention involves:

(a) contacting a double-stranded nucleic acid molecule with a mismatch-specific endonuclease, wherein one strand of said double-stranded nucleic acid molecule has one or more variant nucleotides which create at least one mismatch in the double-stranded nucleic acid molecule so that the double-stranded nucleic acid molecule is cleaved at the 3'-side of the mismatch by the mismatch-specific endonuclease;

(b) ligating a double-stranded linker, containing a 3'-overhang, to the 3'-end of the strand with the one or more variant nucleotides, wherein the 3'-overhang of the linker is degenerate and the double-stranded portion of the linker is of a predetermined sequence; and (c) determining the sequence of the one or more variant nucleotides via the predetermined linker sequence thereby identifying the sequence of the one or more variant nucleotides.

In accordance with some embodiments, the 5'-end of at least one strand of the double-stranded nucleic acid molecule in step (a) is optionally bound to a solid support; the 3'-ends of the double-stranded nucleic acid molecule in (a) are blocked; the strand with the one or more variant nucleotides is labeled; the double-stranded linker is detectably labeled; or the double-stranded nucleic acid molecule of step (a) is produced by a polymerase chain reaction, wherein the polymerase chain reaction is carried out with a universal primer and wherein the 5'-end of the universal primer is optionally bound to a solid support.

Some embodiments provide that the cleaved double-stranded nucleic acid molecule in (b) is denatured and the strand with the one or more variant nucleotides is isolated prior to ligation to the double-stranded linker in step (b).

While particular embodiments provide that step (c) is carried out by sequencing-by-synthesis from the predetermined linker sequence, other embodiments provide that step (c) is carried out by:

(i) denaturing the double-stranded portion of the linker;

(ii) hybridizing a complementary primer to the predetermined linker sequence in the presence of an intercalating fluorescence resonance energy transfer (FRET) donor;

(iii) contacting the product of step (ii) with DNA Polymerase and at least one ddNTP labeled with a FRET acceptor to extend the complementary primer; and (iv) detecting FRET, wherein the presence of FRET is indicative of the sequence of the variant nucleotide.

A kit for identifying the sequence of one or more variants in a nucleic acid molecule is also provided by the present invention. Such a kit includes a mismatch-specific endonuclease that cleaves a double-stranded nucleic acid molecule at the 3'-side of a mismatch; and a double-stranded linker, containing a 3'-overhang, wherein the 3'-overhang of the linker is degenerate and the double-stranded portion of the linker is of a predetermined sequence. In certain embodiments, the kit further includes a primer complementary to the predetermined sequence of the linker; an intercalating FRET donor; and ddCTP, ddATP, ddTTP, and ddGTP each labeled with a different FRET acceptor.

BRIEF DESCRIPTION OF THE DRAWINGS

FIG. 2 depicts schematics of a method of the present invention, wherein either the variant nucleic acid molecule (FIG. 2A) or reference nucleic acid molecule (FIG. 2B) is attached to a solid support such as streptavidin-coated magnetic beads via biotin. To prevent ligation of the double-stranded linker to the reference non-cleaved nucleic acid molecule, the free 3'-OH groups can be capped prior to mismatch-specific endonuclease cleavage.

FIG. 5 shows chromatograms of the nucleic acid sequences upstream (FIG. 5A) and downstream (FIG. 5B) of mismatches between a variant and reference sequence in Control G/C which was captured, amplified and sequenced. The nucleotides at the mismatch and the linker sequence are indicated. Mismatch, linker and linker sequence (including the mismatch) are shown.

DETAILED DESCRIPTION OF THE INVENTION

Figure 1:
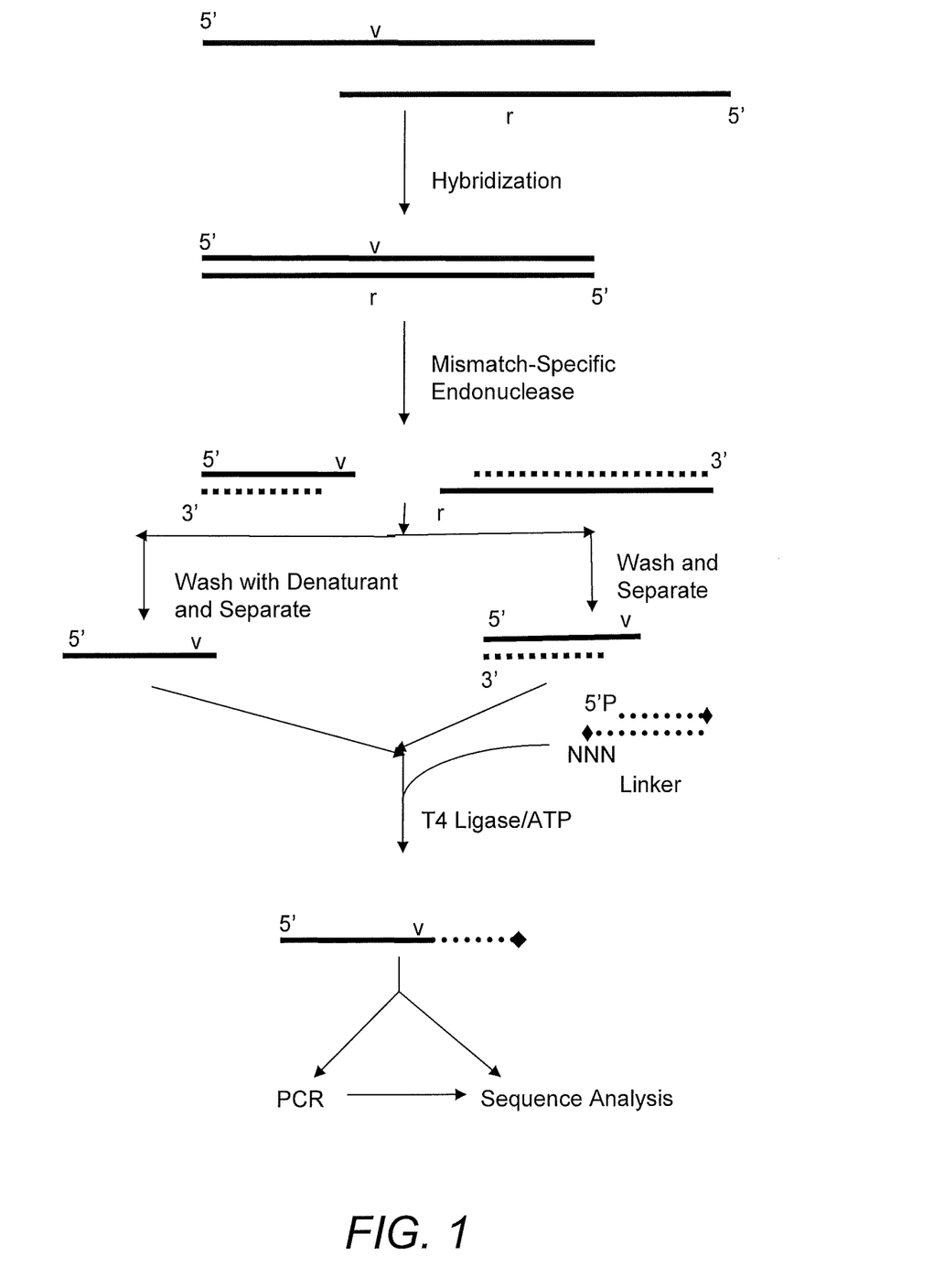
FIG. 1 shows a schematic of the method of the present invention. The DNA strands represented by the solid-lines contain the nucleotides involved in the mismatch at their 3'-ends. The variant nucleotide is indicated by v, the reference nucleic acid with reference nucleotide r is also indicated. The degenerate double-stranded linker is ligated to the 3'-end of the cleaved mismatch. In this instance three base degeneracy is indicated by the bases NNN.

It has now been found that a randomized double-stranded linker can be used to capture a single, mismatch-specific endonuclease cleavage product along with its mismatch cut-site 3'-overhang with no a priori knowledge of the sequence at the 3'-mutation end. Advantageously, the instant method provides both the identification of the sequence of the variant nucleotide, as well as the context of the mutation. In this regard, the present invention provides a rapid method for the parallel detection and identification of variations in nucleic acid molecules. While it is contemplated that one or more variations can be readily detected and identified using the instant method, for simplicity and clarity, FIG. 1 depicts the method of the invention in the identification of a single nucleotide polymorphism or mutation. As shown in FIG. 1, a single-stranded sample nucleic acid molecule containing nucleotide variation (v) is hybridized with a single-stranded reference or wild-type nucleic acid molecule with reference nucleotide (r) to produce a double-stranded nucleic acid molecule with a mismatch. Upon contact of the double-stranded nucleic acid molecule with a mismatch-specific endonuclease, the double-stranded nucleic acid molecule is cleaved at the 3'-side of the mismatch. Because direct sequence analysis of the resulting molecule is confounded by the fact that the bases of most interest are at the very tip of the 3'-end, the instant method provides attaching a linker to the 3'-end of the cleaved variant nucleic molecule. To preserve the variant nucleotide at the 3'-end, the linker is double-stranded and contains a randomized or degenerate 3'-overhang to facilitate the efficiency of annealing to the variant single-stranded nucleic acid molecule. Advantageously, the double-stranded portion of the linker is of a pre-determined sequence (e.g., a universal sequence) thereby providing a site for a primer (e.g., a universal primer) to anneal for polymerase chain reaction (PCR) and/or sequence analysis of the variant nucleotide immediately adjacent to the linker sequence.

In accordance with the present method, the double-stranded or duplex nucleic acid molecule is formed by hybridizing a single-stranded sample or variant nucleic acid molecule (e.g., containing, or suspected of containing, a SNP or mutation) with a complementary or nearly complementary single-stranded reference molecule (e.g., a molecule with a known or wild-type sequence) such that any differences form a mismatch. The double-stranded molecule can be produced by restriction endonuclease cleavage of genomic or cDNA molecules, PCR amplification, or a combination thereof, followed by conventional mixing, denaturation and annealing conditions.

In the preparation of the starting material, it is contemplated that adaptamers, which contain a 5'-end followed directly by a template-specific end, or linkers with specific 'sticky ends' (e.g., to anneal to restriction endonuclease sites) can be used to facilitate the direct PCR amplification of sample and reference nucleic acid molecules. Alternatively, sample and reference nucleic acid molecules can be amplified by conventional cloning techniques. When employing PCR, in particular in the amplification of a cloned DNA molecule or a DNA molecule with linker or adaptamer sequences attached thereto, certain embodiments of the present invention embrace the use of universal primers which anneal to vector, linker or adaptamer sequences. In this regard, universal primers, preferably with distinct sequences, are used to initially amplify the sample and reference nucleic acid molecules. Such universal primers and sequences are well-known in the art and include, but are not limited to M13(−20), T7 and the like.

Figure 2A:
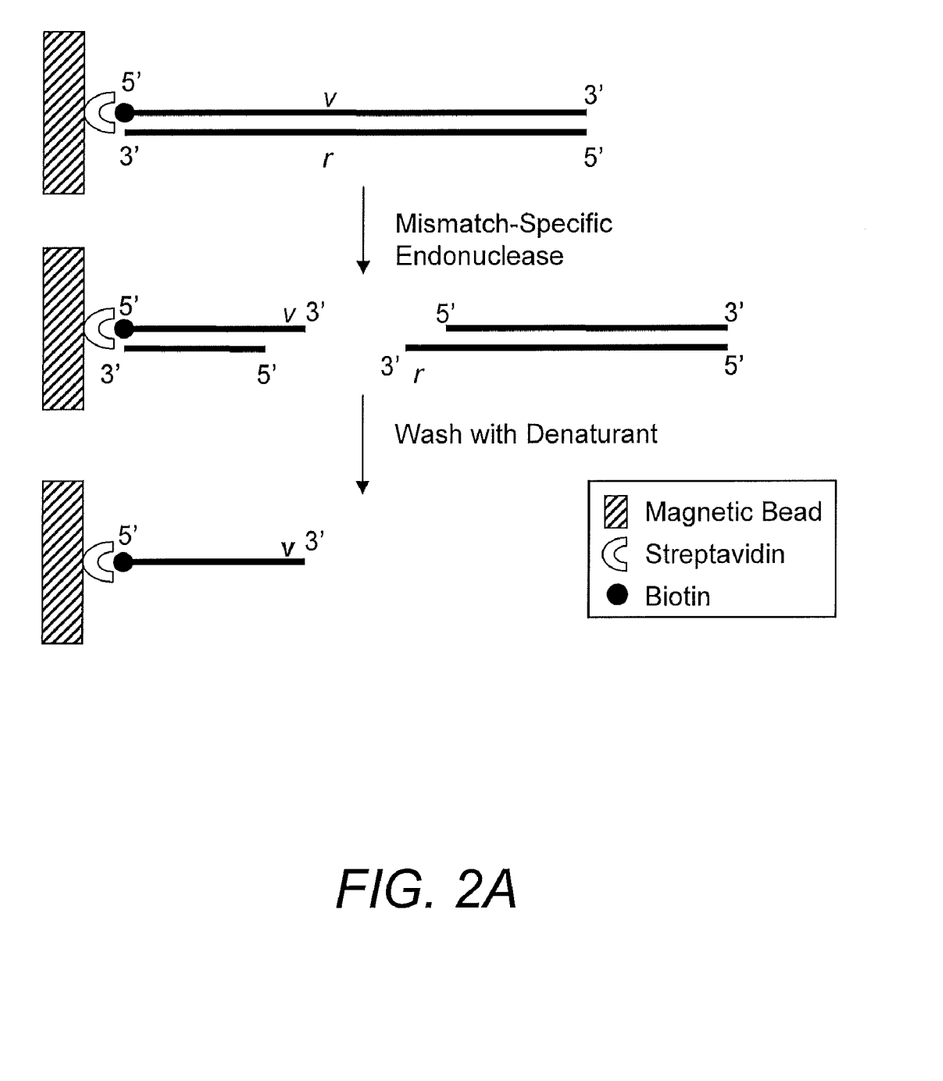

When it is desirable to isolate the single-stranded sample and/or reference nucleic acid molecules, some embodiments embrace immobilization of the single-stranded sample and/or reference nucleic acid molecules on a solid support. Immobilization on a solid support can be accomplished by attaching a functional group to the 5'-end of the nucleic acid molecule, wherein the functional group interacts strongly with a non-soluble entity such as a solid surface, particle, bead or gel. For example, a hydrophobic group on the 5'-end of the nucleic acid molecule can be used to immobilize the nucleic acid molecule on a hydrophobic bead. Covalent attachment via thiol- or amino-derivatized nucleotides to a reactive surface is also contemplated. By way of illustration, FIG. 2A depicts a biotinylated single-stranded sample nucleic acid molecule immobilized on a streptavidin-coated, magnetic bead, wherein upon hybridization to a reference molecule and cleavage by a mismatch-specific endonuclease, the single-stranded sample nucleic acid molecule containing the variant nucleotide can be readily isolated. Alternatively, it is contemplated that the reference molecule can be immobilized such that upon cleavage by a mismatch-specific endonuclease and subsequent denaturation, the double-stranded reference nucleic acid molecule can be removed, leaving the sample nucleic acid molecule free in solution. See FIG. 2B. In accordance with this embodiment, the 3'-end of reference molecule annealed to the sample nucleic acid molecule containing the variant nucleotide can be blocked or capped to prevent subsequent linker ligation.

The attachment of functional groups to nucleic acid molecules is routinely carried out in the art and any suitable method can be employed. However, in particular embodiments, the functional group is attached to a universal primer used in the PCR amplification of the sample and/or reference nucleic acid molecule.

Hybridization of single-stranded sample and reference nucleic acid molecules can also be carried out using routine methods and conditions. Particular embodiments, however, embrace the use of quantitative strand exchange methods. An example of such a method is disclosed, e.g., by Arguello, et al. (1997) *Nucl. Acids Res.* 25:2236-2238). When two nearly identical sequences of double-stranded DNA are denatured and annealed, the yield of heteroduplex can be variable. Purely random annealing can lead to the highest yield $(x+y) \cdot (x+y)$, where x is the amount of one species and y is the amount of the second species. This gives the $xy+yx+x^2+y^2$ distribution of two heteroduplices (xy and yx) and two homoduplices ($x^2$ and $y^2$). If x=y then the 1:1:1:1 ratio is produced. However, this maximum yield is often not attained. For example, if the two sequences have a large number of mismatches, then the melting temperatures of the heteroduplices are much reduced compared to the homoduplices and they will not form at temperatures at which the homoduplices are almost fully annealed. Thus, stringent annealing of homoduplices can be virtually complete during cooling before heteroduplices have the chance to form.

As indicated, particular embodiments of the present invention embrace capping or blocking pre-existing 3'-OH groups of nucleic acid molecules prior to mismatch-specific endonuclease cleavage so that linker ligation to these pre-existing 3'-OH groups is prevented. Any conventional capping or blocking group can be employed. For example, capping can be achieved by untemplated extension with a dideoxy base such as that produced by the enzyme terminal transferase together with a ddNTP. Capping with terminal transferase involves contacting the nucleic acid molecule of interest with any one of the dideoxyNTPs in the presence of terminal transferase so that the enzyme adds a ddNTP to the 3'-OH, thereby preventing ligation to the 3'-OH group.

As an alternative to capping with terminal transferase, a capping adaptor can be employed, wherein said adaptor has a sequence which is different from the double-stranded linker which is ligated to the mismatch-specific endonuclease cleavage product. To facilitate the synthesis of such an adaptor, it is contemplated that the adaptor can have a hairpin structure.

As indicated, a mismatch-specific endonuclease of use in accordance with the present invention desirably cleaves double-stranded nucleic acid molecules on the 3'-side of a mismatch. Exemplary mismatch-specific endonucleases include, but are not limited to, CEL-I and CEL II, and the like. Such enzymes are known in the art and commercially available from sources such as Transgenomics (Omaha, Nebr.).

Alternatively, a free 3'-OH can be generated at a mismatch by depolymerization and pyrophosphorylation as described in WO 02/086169 and U.S. Pat. No. 7,247,428, incorporated herein by reference. In this approach, a nucleic acid molecule of interest is depolymerized from the original intact 3'-OH end back to the mismatch site by pyrophosphorylation with a polymerase enzyme driven to catalyze the reverse of the normal polymerization by a large excess of pyrophosphate. The fact that mismatched bases are not a substrate of this pyrophosphorylation activity is exemplified by the PROMEGA READIT genotyping kit (see, Tsongalis, et al. (2001) *Exper. Mol. Pathol.* 71:222-225).

Figure 2B:
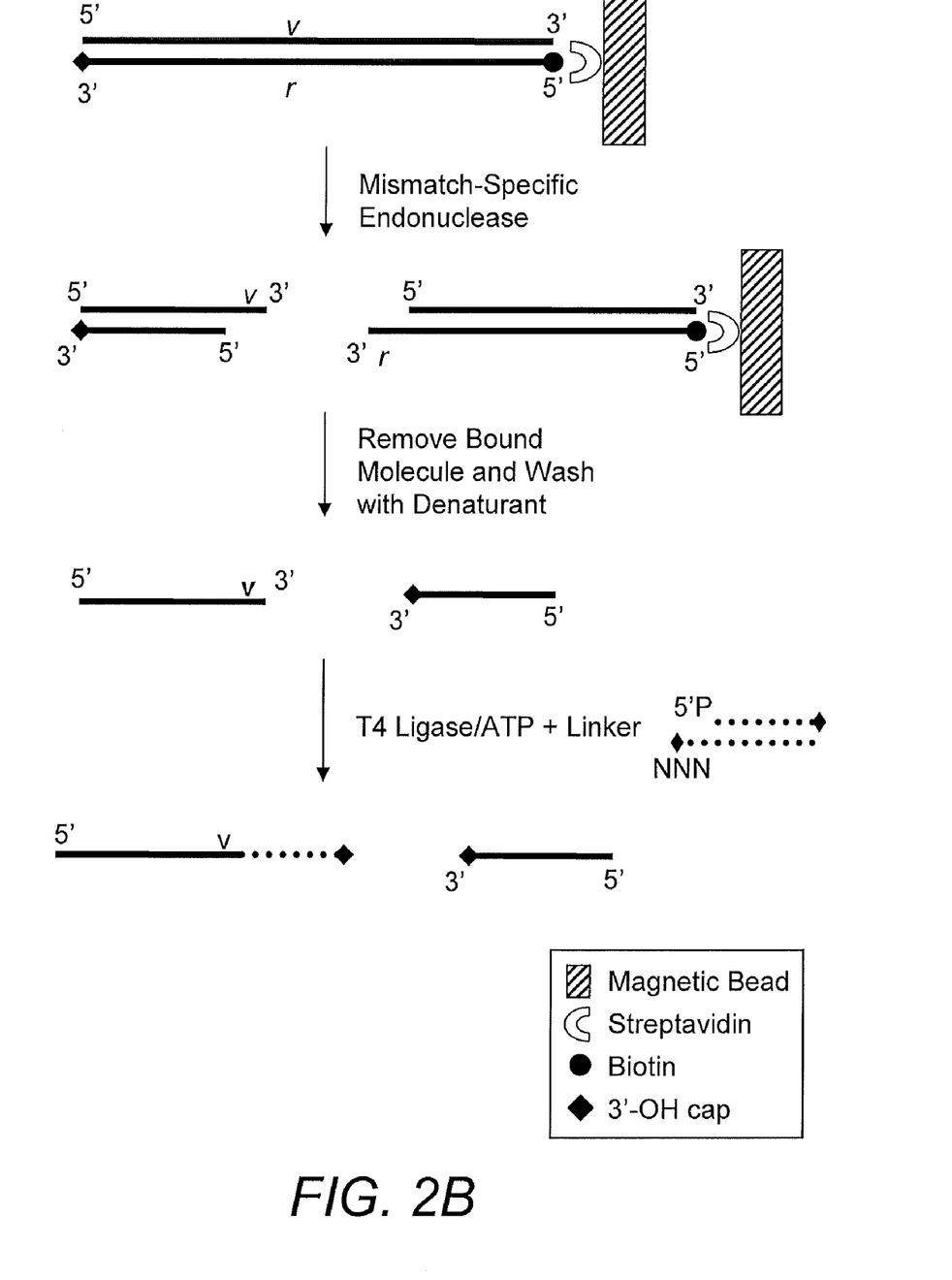

After cleaving the double-stranded nucleic acid molecule (i.e., the heteroduplex), the nucleic acid molecule containing one or more variant nucleotides, also referred to herein as the variant single-stranded nucleic acid molecule or sample nucleic acid molecule, can be directly ligated to the double-stranded linker without being isolated from the other strand of the double-stranded nucleic acid molecule or alternatively isolated from the other strand. As depicted in FIG. 1, isolation of the variant single-stranded nucleic acid molecule can involve washing with a denaturant to generate single-stranded molecules and separating the single-stranded molecules. Such separation can be carried out using conventional size separation procedures or alternatively by tagging the single-stranded molecules. By way of illustration, FIG. 2A shows that when the variant single-stranded nucleic acid molecule is bound to a solid support, denaturation and washing will remove the unwanted molecules thereby isolating the variant single-stranded nucleic acid molecule. Similarly, certain embodiments embrace labeling the 5'-end of the variant single-stranded nucleic acid molecule with a detectable label to facilitate the identification and isolation of said molecule in, e.g., size fractionation methods such as the WAVE platform (Transgenomics, Omaha, Nebr.) or gel electrophoresis. For example, the preparative capability of the WAVE platform can be employed by injecting the denatured product into the WAVE for analysis and collection of the peak corresponding to the labeled variant nucleic acid molecule. Detectable labels can include, e.g., biotin, a fluorophore, a chromophore or the like. Such labels can be incorporated into the variant nucleic acid molecule using conventional methods, e.g., using a labeled universal primer. Alternatively, FIG. 2B shows that when the reference molecule is bound to a solid support, the variant single-stranded nucleic acid molecule can be obtained free in solution. Because the variant single-stranded nucleic acid molecule illustrated in FIG. 2B is found in solution with a 3'-capped reference molecule, "isolated" or "isolating" in the context of this method step does not preclude the presence of other molecules. However, it is desirable that when other molecules are present, said other molecules do not participate, inhibit, or alter subsequent method steps.

Subsequently, a double-stranded linker, containing a 3'-overhang, is ligated to the 3'-end of the isolated variant single-stranded nucleic acid molecule. Specific features of the double-stranded linker are depicted in FIG. 1 and include: a duplex DNA composed of two complementary oligonucleotides, wherein this complementary or double-stranded portion is of a predetermined sequence (e.g., a universal sequence of approximately 6 to 50 nucleotides); a 3'-overhang on the lower strand of the duplex composed of 1, 2, 3, 4, 5, or 6 nucleotides, wherein the overhang is degenerate in nature so that the linker can ligate to all possible cleavage sites; a phosphorylated 5'-end on the upper strand of the duplex; and optionally the 3'-end of the upper strand or the 3'-end of the lower strand are blocked or capped (e.g., with a 3'-amino functional group or dideoxyNTP) to prevent further ligation. Alternatively, the 3'-end of the lower strand can remain free such that it can be extended later by a polymerase. Optionally, a functional group such as biotin can be included on the upper strand of the linker so that it can be captured easily with, e.g., streptavidin-coated surfaces. Moreover, particular embodiments embrace a linker with a hairpin structure (See FIG. 3).

Such double-stranded linkers have been described in the art for use in randomized terminal linker-dependent PCR (RD-PCR) detection of DNA damage. See, e.g., Zhang & Heng (2002) *Biomed. Environ. Sci.* 15:203-8; Rao, et al. (2005) *J. Sichuan Univ. (Med. Sci. Edi.)* 36:779-781; Wu & Heng (2006) *J. Sichuan Univ. (Med. Sci. Edi.)* 37:33-34. When employing a two nucleotide 3'-overhang on the double-stranded linker, a mixture of just 16 molecules would be required, while 3 nucleotides would require 64 molecules, and 4 nucleotides would require 256 molecules. It is contemplated that as many as 6 degenerate nucleotides (i.e., 4096 molecules) can be employed as equal concentrations are not essential. However, in particular embodiments, a two or three nucleotide 3'-overhang is employed. In this regard, a kit containing a double-strand linker with a three nucleotide 3'-overhang could include a mixture of the double-stranded molecules, e.g., as exemplified below.

```
                                              (SEQ ID NO: 1)
     5'-P-TGT AAA ACG ACG GCC AGT-3'-Blocker (SEQ ID NO: 2)
     Blocker-3'-NNN ACA TTT TGC TGC CGG TCA-5'
```

The linker can be ligated to the newly exposed 3'-OH groups (i.e., generated by the mismatch-specific endonuclease) using standard ligation conditions. Such conditions can include the use of the enzyme T4 DNA ligase together with ATP and other components well-known in the art.

Figure 3:
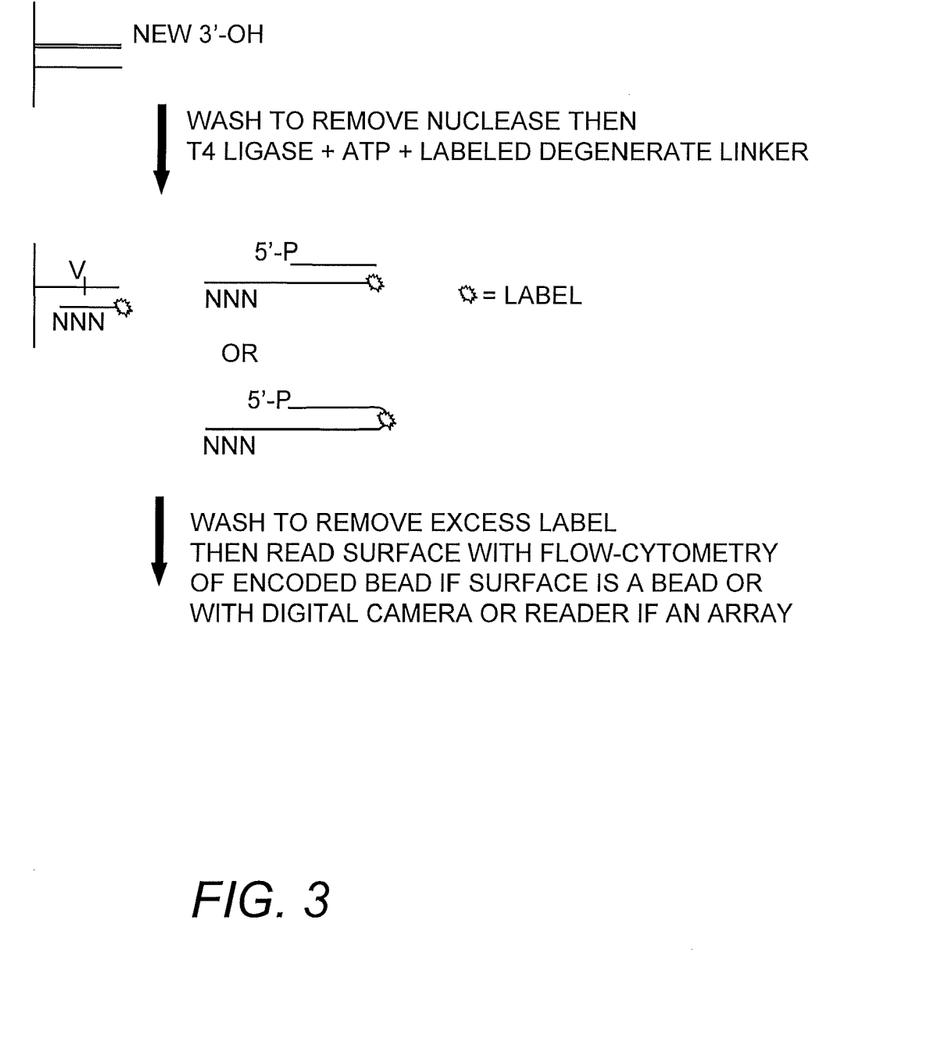
FIG. 3 depicts the use of a labeled linker and a labeled linker with a hairpin for ligation to the variant nucleotide 3' end (v) created by cleavage.

In some embodiments of the present invention, the double-stranded linker is detectably labeled (See FIG. 3). In this regard, the linker contains a label (e.g., a fluorophore or a moiety commonly used in ELISA, such as a biotin functional group which can bind to a streptavidin-horseradish peroxidase conjugate) allowing detection at a low concentration. Ligation of the labeled linker to the newly generated 3'-OH end of an immobilized variant nucleic acid molecule can provide for rapid detection of the presence of a mutation. In this regard, mutations can be detected in batch mode, e.g., by flow-cytometry or an array, permitting high-throughput analysis.

Advantageously, the attached linker is immediately adjacent to the variant nucleotide(s) in the variant single-stranded nucleic acid molecule and provides a means to readily detect and determine the nature of the variant(s). It is contemplated that the resulting linker-ligated variant nucleic acid molecule can be denatured and isolated (e.g., via the WAVE system as described herein), or alternatively, the linker-ligated variant nucleic acid molecule can be directly used in PCR and/or sequence reactions. In this regard, there are a variety of methods which can be used to determine the sequence of the one or more variant nucleotides in the variant nucleic acid molecule. For example, when the starting material is generated by PCR amplification, as disclosed herein, it is contemplated that single-template PCR methods can be employed in combination with conventional sequencing methods to reveal the sequence of the variant nucleotide(s). In accordance with such PCR amplification of the variant nucleic acid molecule, some embodiments embrace the use of two different universal PCR primers, whereas other embodiments embrace the use of a single universal PCR primer which anneals to both the 5'- and 3'-end. Single-template PCR methods, e.g., polony PCR, are known in the art. See, e.g., Mitra & Church ((1999) *Nucleic Acids Res.* 27:e34) and Mitra, et al. ((2003) *Proc. Natl. Acad. Sci. USA* 100:5926-5931), wherein each PCR product that arises represents a homogenous "plonal" product (by analogy to PCR clonal).

Linker-ligated variant nucleic acid molecules or PCR amplicons of the same can be analyzed by Sanger sequencing, PCR-based sequencing or sequencing with a mixture of tagged probes (e.g., fluorescence, mass-tags, etc).

Alternatively, certain embodiments embrace identifying the sequence of the variant nucleotide(s) in a nucleic acid molecule by sequencing-by-synthesis methods such as pyrosequencing, GENOME SEQUENCE 20 DNA sequencing system (GS20, Roche/454 Life Sciences; Margulies, et al. (2005) *Nature* 43:376-380), or Solexa sequencing (Illumina; Robertson, et al. (2007) *Nature Methods.* 4(8):651-7). In pyrosequencing, a primer that is complementary to the predetermined linker sequence is annealed to the linker-ligated variant nucleic acid molecule and the first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge-coupled device (CCD) camera and seen as a peak in a PYROGRAM, wherein each light signal is proportional to the number of nucleotides incorporated. Apyrase, a nucleotide degrading enzyme, continuously degrades unincorporated dNTPs and excess ATP. When degradation is complete, another dNTP is added. Addition of dNTPs is performed one at a time. As the process continues, the complementary DNA strand is built up and the nucleotide sequence is determined from the signal peak in the PYROGRAM. Because the mutation is immediately adjacent to the linker, sequence analysis of 100 bp would be sufficient to both identify the sequence of the SNP or mutation and identify the location of the variant nucleic acid molecule in the genome or gene. The Solexa sequencing-by-synthesis platform uses reversibly terminated, fluorescently labeled dNTPs to sequence immobilized DNA templates in massively parallel fashion. It is contemplated that gene or genome-wide analysis can be performed using the instant method in combination with a massively parallel sequence-by-synthesis format.

Figure 4:
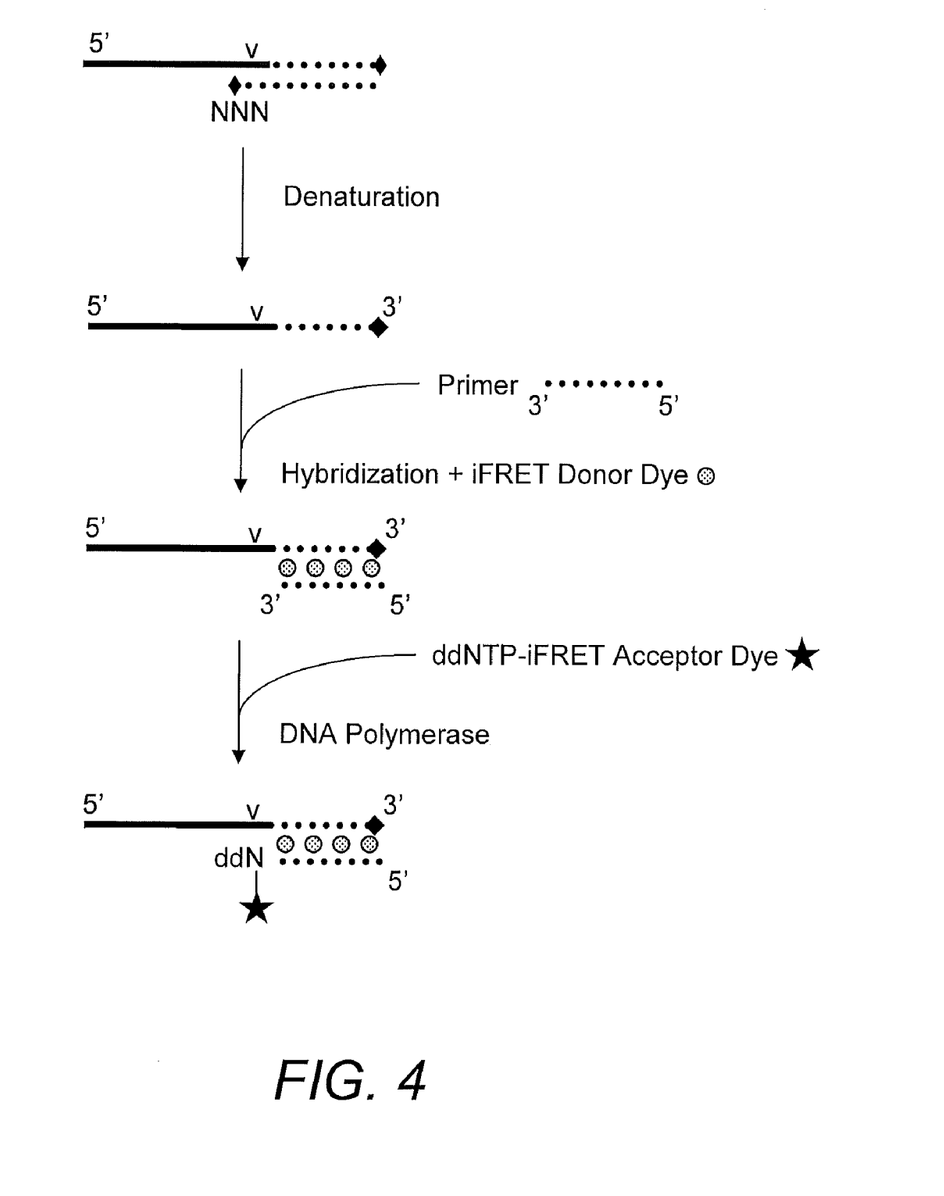
FIG. 4 shows a schematic of a single-base extension approach to determining the sequence of a variant nucleotide (v) adjacent to a linker.

In still other embodiments, the sequence of the variant nucleotide in a nucleic acid molecule is identified using a single-base extension or mini-sequencing approach (see, e.g., Takatsu, et al. (2004) *Nucl. Acids Res.* 32:e156). As depicted in FIG. 4, this approach involves denaturing the double-stranded portion of the linker, which is ligated to the single-stranded variant nucleic acid molecule and hybridizing a complementary primer to the predetermined linker sequence in the presence of an intercalating fluorescence resonance energy transfer (FRET) donor such as SYBR green I. Subsequently, the FRET donor-labeled molecule is contacted with DNA Polymerase and a mixture of ddCTP, ddATP, ddTTP, and ddGTP, each labeled with a different FRET acceptor (e.g. Rox or Cy5), to extend the complementary primer. Depending on the nucleotide incorporated, a different wavelength of light will be emitted (i.e., base-specific fluorescence) and therefore reveal the sequence of the variant nucleotide. For example, Rox emits an orange fluorescence upon excitation by the green light emitted by SYBR Green I, whereas red fluorescence is emitted from Cy5 upon excitation by SYBR Green I.

Still other embodiments provide that the variant nucleotide(s) is determined by:

(i) PCR amplification of the nucleic acid molecule using a primer specific to the molecule and another primer specific to the predetermined linker sequence, and (ii) sequencing by termination using either a sequencing primer specific to the predetermined double-stranded linker, or specific to the nucleic acid molecule.

When the identification of more than one variant nucleotide is required, additional primers can be used in combination with a single-base extension approach. For example, on the basis of the nucleotide revealed by the first primer extension reaction, a subsequent, overlapping primer can be generated with one base more on its 3'-end which is complementary to the revealed nucleotide. There are four possibilities A, C, G or T thereby requiring only a modest increase in the number of extended primers which need to be generated. The next nucleotide can then be determined, wherein the process can be repeated with sixteen primers, and sixty four primers, etc. When applied sequentially and on the basis of the previous bases revealed, four steps using four primers will reveal the four bases at the 3'-OH end of the variant nucleic acid molecule.

Alternatively, a mini-sequencing method can be employed wherein instead of using all four ddNTPs in a mixture, one ddNTP is used in combination with three dNTPs. Mini-sequencing and primer extension methods are well-established in combination with the WAVE platform and the use of a mixture of 20 parts of a single ddNTP and 80 parts dNTPs yields a short sequencing run allowing approximately 20 nucleotides of sequence to be determined beyond the universal primer in a short 10 minute analysis.

The key novelty of the instant invention is the extension of the variant nucleotide itself, with a known sequence. This juxtaposition of the variant to the linker readily allows rapid processing by PCR and/or sequence analysis. While the prior art provides various methods for extending 3'-ends, including blunt-end ligation with a linker (see, U.S. Patent Application No. 2003/0022215) and the use of terminal transferase enzyme to extend the 3'-OH by polymerization with deoxynucleotide-triphosphates, the present invention offers advantages over these prior art methods. For example, because mismatch-specific endonucleases create a 3'-OH overhang, the creation of the blunt-end for ligation of the linker would actually remove the variant nucleotide of interest. Thus, while the relative location of the mutation could be identified, the sequence of the variant nucleotide could not be determined. Moreover, the yield of blunt-end ligation is lower than that of ligation to overhangs. A disadvantage of using terminal transferase is that a homopolymer of undefined length is created at the 3'-end leading to a range of fragment sizes in subsequent processes such as PCR and sequencing. Moreover, it would be nearly impossible to know from sequence analysis where the homopolymer begins if the cleavage site itself contains the same base as that used for creating the extension.

Moreover, while regular Sanger sequencing can be employed, the use of sequencing-by-synthesis methods has particular utility in combination with the present method because the read length limitation of sequencing-by-synthesis technologies is not a handicap. If for example pyro-sequencing is employed, approximately 25 rounds of pyro-sequencing would be sufficient to identify the variant nucleotide and its context. In this regard, the prior art does not provide this integration of minimal sequencing with mismatch-specific endonuclease cleavage. As such, the present method finds application in SNP detection, mutation detection, methylation detection (via bisulfite treatment of genomic DNA), detecting variation between alleles, between individuals, between normal and diseased tissue, between species and for detection of induced mutations.

Moreover, it is contemplated that the instant method can be employed in a whole gene application, wherein many amplicons covering all exons and promoter sites could be mixed together. The mixture could be achieved by multiplex PCR using a universal primer or could be mixed just prior to attachment of the linker. In either case a single injection onto a WAVE System can be used to reveal all variants in one or more genes. Using the solid-phase approach (i.e., the use of a solid support) there will only be one cleavage product per variant and no intact uncleaved fragment. The nucleic acid molecules in the separated peaks can be collected and cycle-sequenced or subjected to pyrosequencing or other highly parallel sequencing-by-synthesis methods. The results can be used to identify the gene location from which the cleavage fragment originated and the variation present at the location adjacent to the linker.

The invention is described in greater detail by the following non-limiting examples.

EXAMPLE 1

Materials and Methods

Materials. SURVEYOR nuclease (CEL II) was purified from celery by a modification of known methods (Yang, et al. (2000) supra; Gerard, et al. (2006) supra). Enzymatic activity was assigned based upon a denatured DNA solubilization assay performed at pH 8.5 (Yang, et al. (2000) supra). One unit of solubilization activity was defined as the amount of enzyme required to produce 1 ng of acid-soluble material in 1 minute at 37° C.

OPTIMASE® Polymerase and MAXIMASE™ Polymerase were from Transgenomic, Inc (Omaha, Nebr.). M-280 Streptavidin magnetic DYNABEADS® were from Dynal Biotech (INVITROGEN, Carlsbad, Calif.). Cloned T4 DNA ligase was prepared by Transgenomic, Inc. Streptavidin was purchased from SIGMA (Sigma/Aldrich, St. Louis, Mo.). Control G and Control C plasmids were from Transgenomic, Inc. Control C and Control G have inserts (632 bp) that differ at a single base pair, so that annealing of their PCR products produces heteroduplices that when cleaved by SURVEYOR nuclease produce cleavage products 415 and 217 bp long.

Oligonucleotides. Oligonucleotides were synthesized by Sigma-Genosys (The Woodlands, Tex.). Unless indicated otherwise, oligonucleotides were desalted before use.

Oligonucleotides used in the study included: pCEL190F30, 5'-ACA CCT GAT CAA GCC TGT TCA TTT GAT TAC-3' (SEQ ID NO:3); pCEL190F30-5'Bio, 5'-Biotin-ACA CCT GAT CAA GCC TGT TCA TTT GAT TAC-3' (SEQ ID NO:4); pCEL81OR25, 5'-CCA AAG AAT GAT CTG CGG AGC TTC C-3' (SEQ ID NO:5); pCEL81OR25-5'Bio, 5'-Biotin-CCA AAG AAT GAT CTG CGG AGC TTC C-3' (SEQ ID NO:6); M13RDPCRtop, 5'-P0$_4$-CGA CTG GAG CAC GAG GAC ACT ACT GGC CGA CGT TTT ACA CC-NH$_4^+$-3' (SEQ ID NO:7); M13RDPCR3Nbottom, 5'-GGT GTA AAA CGA CGG CCA GTA GTG TCC TCG TGC TCC AGT CGN NN—NH$_4^+$-3' (SEQ ID NO:8); M13RDPCR2Nbottom, 5'-GGT GTA AAA CGA CGG CCA GTA GTG TCC TCG TGC TCC AGT CGN N—NH$_4^+$-3' (SEQ ID NO:9); M13RDPCR1Nbottom, 5'-GGT GTA AAA CGA CGG CCA GTA GTG TCC TCG TGC TCC AGT CGN—NH$_4^+$-3' (SEQ ID NO:10); M13uniPCR, 5'-GGT GTA AAA CGA CGG CCA GTA GTG TCC TCG TG-3' (SEQ ID NO:11); pCEL324F21, 5'-CCA TGG TAA GGA TAT GCA CTC-3' (SEQ ID NO:12); pCEL490R22, 5'-GAG TTT CGC CAG ATT CAA CAT C-3' (SEQ ID NO:13). Triple degenerate linkers are sufficient for ligation to all possible sites, however a mixture of single, double and triple degenerate linkers was used in this protocol.

PCR Amplification Conditions of DNA for Annealing and Binding to Streptavidin Magnetic Beads. A 632-bp region from Control C or Control G plasmid was amplified using 10 ng of template (either Control C or Control G plasmid), 66 ng of pCEL190F30-5'Bio, 33 ng of pCEL190F30, 66 ng of pCEL81OR25-5'Bio, 33 ng of pCEL81OR25, 0.2 mM of each dNTP, and 0.5 μL of OPTIMASE Polymerase (6 U/μL) in 1×

OPTIMASE Reaction Buffer (10 mM Tris-HCl, pH 8.8, 75 mM KCl, 1.5 mM MgCl$_2$, and 0.01% (V/V) TRITON X-100).

Amplification of Ligated Cleavage Products Eluted from Streptavidin Magnetic Beads. The 418-bp fragment upstream from the SURVEYOR nuclease cleavage site in Control G/C heteroduplices was amplified using 1 µL of ligation reaction mix as template, 100 ng of pCEL190F30, 100 ng of M13uniPCR, 0.2 mM of each dNTP, and 0.5 µL OPTIMASE Polymerase (6 U/µL) in 1× OPTIMASE Reaction Buffer. The 216-bp fragment downstream from the SURVEYOR Nuclease cleavage site in Control G/C heteroduplices was amplified using 1 µL of ligation reaction mix as template, 100 ng of pCEL81OR25, 100 ng of M13uniPCR, 0.2 mM of each dNTP, and 0.5 µL of OPTIMASE Polymerase (6 U/µL) in OPTIMASE Polymerase Buffer.

PCR Amplification Cycling Parameters. PCR amplifications were carried out in a heated-lid thermocycler using the following program: 95° C. for 2 minutes; 30 cycles of 95° C. for 30 seconds, 63.8° C. for 30 seconds, and 72° C. for 70 seconds; and finally 72° C. for 5 minutes.

Annealing of Amplified PCR Products. Annealing, using a thermocycler, was performed as follows. Equal amounts of Control C and Control G PCR products in PCR reaction components were mixed; denatured at 95° C. for 2 minutes and cooled at a rate of −2° C./second until the temperature reached 85° C., and then cooled at a rate of −0.1° C./second to 25° C. Samples were then held at 4° C.

Binding of Amplified, Annealed PCR Products to Streptavidin Magnetic Beads. Annealed Control G/C PCR products (10 µL; ~400 ng) were mixed with 10 µL of 10 mg/mL M-280 Streptavidin DYNABEADS magnetic beads stabilized in 2 M NaCl and 10 mM Tris-HCl (pH 8) and incubated at room temperature for 10 minutes. Samples were then washed twice with 40 µL of 1M NaCl and 5 mM Tris-HCl (pH 8) and twice with 40 µL of 1× OPTIMASE Reaction Buffer, and resuspended in 20 µL of 1× OPTIMASE Reaction Buffer.

SURVEYOR Nuclease Digestion. Annealed Control G/C PCR products (200 ng) in 1× OPTIMASE Reaction Buffer were incubated in the presence of 1.5 mM or 10 mM MgCl$_2$ (as indicated), 1 µL of SURVEYOR nuclease (5 U/µL) and 1 µL of T4 DNA ligase (ENHANCER S) at 42° for 20 minutes. Digestion was stopped with 1/10 volume of 0.5 M EDTA (pH 8.0) and the DNA present in the supernatant was precipitated with 3 volumes of ethanol and resuspended in 10 µL 1 mM Tris-HCl and 0.1 mM EDTA (pH 8).

Linker Preparation M13RDPCRtop (15 µg), 5 µg M13RDPCR3Nbottom, 5 µg M13RDPCR2Nbottom and 5 µg M13RDPCR1Nbottom were mixed in 50 mM NaCl, 10 mM Tris-HCl (pH 8), and 1 mM EDTA (pH 8) to a final concentration of 0.91 µg/µL. The mixture was denatured at 94° C. for 4 minutes, cooled at a rate of −0.1° C./second until the temperature reached 73° C., kept at 73° C. for 30 minutes and cooled at a rate of −0.1° C./second until the temperature reached 16° C.

Ligation of Digested DNA and Linker. SURVEYOR nuclease-digested DNA samples (5 µL; 50-100 ng) were mixed with 560 ng of linker and 400 units (cohesive end ligation units) of T4 DNA ligase (400 U/µL) in ligation buffer (66 mM Tris-HCl, pH 7.6, 10 mM MgCl$_2$, 1 mM ATP, 1 mM DTT) containing 7.5% (w/v) PEG 6000 in a final volume of 20 µL and incubated at 16° C. for 60 minutes. Ligation was stopped by incubation at 65° C. for 10 minutes.

DNA Sequence Analysis. The 415-bp and the 217-bp fragments produced by SURVEYOR nuclease cleavage of Control G/C heteroduplices were ligated to linker and amplified as described herein. Each amplified DNA was purified by using a QIAQUICK PCR Purification Kit (QIAGEN, Valencia, Calif.), Quick-Step PCR Clean-up System (Edge BioSystems, Gaithersburg, Md.) or was isolated by subjecting the DNA to agarose gel electrophoresis (1.75% agarose), cutting the DNA band from the gel, and cleaning up the DNA using a QIAGEN Gel Clean-up System (QIAGEN, Inc., Valencia, Calif.). Purified DNA fragments (20 ng) were subjected to cycle sequencing using 2.5 pmole of primer pCEL324F21, pCEL190F30, pCEL490R22, or pCEL81OR25, 5 µL Better DAF5 Buffer (The Gel Company, San Francisco, Calif.), and 0.5 µL Big Dye Mix (Applied Biosystems, Foster City, Calif.). Reactions were denatured at 95° C. for 4 minutes followed by 25 cycles of 95° C. for 30 seconds, 54° C. for 1 minute and 72° C. for 4 minutes, and then extended at 72° C. for 5 minutes. Sequencing products were purified using CLEAN-SEQ magnetic beads (Agencourt, Beverly, Mass.) according to the manufacturer's instructions and analyzed in a 3100 Genetic Analyzer (Applied Biosystems, Foster City, Calif.).

EXAMPLE 2

Capturing 3'-Overhang Nucleotides Generated by Mismatch Endonuclease Using Randomized Terminal Linker-Dependent PCR Requirements for Capturing the 3'-Overhang Nucleotides Generated by SURVEYOR Nuclease at Mismatch Cut Sites. Direct sequence analysis of SURVEYOR nuclease cleavage products involves the capture of the 3'-overhangs created after digestion at a mismatch site. The capture must be specific to eliminate background during the subsequent sequencing reaction. The main challenge comes from background produced as the result of the 5'-to-3' exonuclease activity of SURVEYOR nuclease (Gerard, et al. (2006) supra) attacking the ends of PCR products. After digestion of a Control G/C heteroduplex with SURVEYOR nuclease, cleavage fragments (415 bp and 217 bp) are present in a mixture along with undigested homoduplices and heteroduplices (632 bp) and the 5'-to-3' exonuclease activity of SURVEYOR nuclease creates 3'-overhangs at both ends of the full-length molecules that will compete for capture with the specific 3'-overhangs of the digested fragments created from the internal cut at the mismatch.

To increase the specificity of capturing the 3'-overhang at the mismatch cut site, the digested fragments in the DNA population were specifically enriched after the SURVEYOR nuclease digestion using streptavidin magnetic beads. Introduction of biotin at the 5'-ends of a PCR fragment and subsequent binding to streptavidin attached to beads protected the 5'-ends of the fragment from SURVEYOR 5'-to-3' exonuclease. Therefore, this method can be used to prevent capture of the ends of full-length molecules.

Given a method to protect PCR product ends and to produce only mismatch 3'-overhangs in SURVEYOR nuclease-treated DNA, a method for capturing and amplifying those 3'-ends was developed.

Enrichment of SURVEYOR Nuclease Digestion Products Using Streptavidin Magnetic Beads. Two sets of identical 632-bp Control G and Control C DNA fragments were amplified with a mixture of four primers as described in Example 1. This produced an equal mixture of four different products for each template: molecules with biotin at both 5'-ends, with biotin at the 5'-end of the upper strand, with biotin at the 5'-end of the lower strand and molecules without biotin. Equal amounts of the two reactions were mixed, annealed and bound to streptavidin magnetic beads. The resulting beads were washed to eliminate non-specific binding of DNA and treated with SURVEYOR nuclease in the presence of ENHANCER and 1.5 mM $MgCl_2$ or 10 mM $MgCl_2$. The digested products were then eluted from the beads to capture digestion fragment 3'-overhangs. It is important to realize that in this method only 50% of the molecules are heteroduplices and 50% of the heteroduplices are lost because they lack biotin and don't bind to streptavidin or because they have biotin at both ends and don't get released from the streptavidin magnetic beads after the digestion. Thus, a maximum of 25% of the molecules were available for mismatch detection. In addition, only one of the two cleavage fragments of a heteroduplex bound at one end to streptavidin was released after digestion. However, using this approach all uncut molecules would either be eliminated in the flow-through during washes, or would remain bound to the streptavidin magnetic beads after the digestion, and all products eluted after the SURVEYOR nuclease digestion would have a 3'-overhang derived from a mismatch site.

The validity of the method was tested by comparing SURVEYOR nuclease digestion of annealed Control G/C PCR products either directly or after binding to streptavidin magnetic beads and analyzing the products in a 2% agarose gel. As expected, two digested products of 415 bp and 217 bp corresponding to the cleavage fragments at both sides of the mismatch cut site were visualized in the gel in both samples. However, the results showed an almost complete (>10-fold) elimination of full-length PCR products and a similar enrichment of the digestion fragments when the annealed Control G/C PCR products were digested by SURVEYOR nuclease after binding to streptavidin magnetic beads.

RD-PCR. The capture of the 3'-ends of the cleavage fragments generated by SURVEYOR nuclease digestion is required to provide the sequence identity of the mismatch. RD-PCR was used here to capture the 3'-overhangs produced by mismatch-specific endonucleases at a mismatch (FIG. 1). A linker containing a mixture of oligonucleotides with one, two or three protruding degenerate bases were ligated at the 3'-end (each position containing an equal mixture of A, T, C or G) to SURVEYOR nuclease-digested DNA. One strand of linker subpopulations, carrying bases complementary to the 3'-overhangs created after the SURVEYOR nuclease cut, was annealed to the overhangs. The phosphorylated, receding 5'-end of the complementary strand of the linker was then ligated to the 3'-overhangs of the digested PCR fragments at the mismatch. Formation of dimers between linkers was prevented by adding amino groups to the 3'-ends of both linker strands. The ligation products were then amplified by PCR using a primer complementary to the sequence of Control G/C PCR fragment and another complementary to the linker sequence.

To demonstrate the validity of the method, a Control G/C homoduplex/heteroduplex mixture was generated utilizing PCR products prepared as described in Example 1. The DNA mixture was digested with SURVEYOR nuclease in the absence of streptavidin beads and subjected to the RD-PCR procedure. Analysis of the PCR fragments generated after RD-PCR revealed minor amounts of a 450-bp fragment using pCEL190F30 (a specific primer that anneals to the 5'-end of the Control G/C PCR product) and M13uniPCR (a primer that anneals to the linker sequence) and minor amounts of a 250-bp fragment using pCEL81OR25 (a specific primer that anneals to the 3'-end of the Control G/C PCR product) and M13uniPCR. Since the size of the linker was 41-bp, the sizes of these fragments corresponded to the expected amplified fragment sizes upstream and downstream of the SURVEYOR nuclease cut site. A major 650-bp product was also present in the RD-PCR amplification, produced by amplification of the 632-bp original full-length Control G/C. This was the result of SURVEYOR 5'-to-3' exonuclease activity creating 3'-overhangs at the ends of full-length Control G/C PCR product, allowing ligation of these ends to the linker. These results demonstrated that the RD-PCR linker was ligated successfully to all three types of exposed 3'-overhangs generated by SURVEYOR nuclease in the absence of streptavidin.

Enrichment of SURVEYOR Nuclease Digestion Products Using Streptavidin Magnetic Beads Reduces Amplification of Full-length Molecules after RD-PCR. A Control G/C homoduplex/heteroduplex mixture was again generated using PCR products prepared as described in Example 1. The mixture was bound to strepavidin beads, the beads were washed, the bound DNA was digested with SURVEYOR nuclease, and cleaved fragments were recovered from the supernatant and subjected to RD-RCR as described in Example 1. Agarose gel analysis of the fragments amplified by RD-PCR showed that binding annealed Control G/C PCR products to streptavidin magnetic beads to elute only SURVEYOR nuclease digested fragments prevented amplification of most of the full-length molecules. These results confirmed that this method substantially reduces the number of full-length molecules and enriches cleavage products present after RD-PCR.

DNA Sequence Analysis of Cleavage Fragments Captured by RD-PCR. PCR fragments released from streptavidin magnetic beads after digestion with SURVEYOR nuclease in the presence of 1.5 mM $MgCl_2$ and amplified by RD-PCR were cleaned up with a QIAGEN PCR Purification Kit according to the manufacturer instructions, and were sequenced using a primer positioned at the upstream end of Control G/C PCR product. The amplified DNA was contaminated with a small amount of full-length Control G/C product. DNA sequencing through the 3'-end of the upstream cleavage fragment amplified by RD-PCR and into the linker sequence showed a clean chromatogram up to the mutation point. From this position and for approximately 45 bases, the chromatogram contained mixed sequences that corresponded to a mixture of the full-length Control G/C and linker sequences. After the 45 bases, the sequence was again clean and corresponded to the sequence of full-length Control G/C. It is contemplated that the mixed sequence observed across the linker region was a consequence of the presence of a mixed population of molecules produced by linker ligated to: 3'-overhangs created by SURVEYOR nuclease cutting at the mismatch site and 3'-overhangs created by SURVEYOR nuclease 5'-to-3' exonuclease activity nibbling at the ends of full-length Control G/C molecules. Thus, even though the application of the streptavidin magnetic bead procedure prior to RD-PCR enriches cleavage fragments >100 fold over full-length fragments, some full-length DNA persists to create a secondary pattern during subsequent sequencing of the RD-PCR amplified DNA.

To confirm this, cleavage fragments of the appropriate size from Control G/C were eluted from streptavidin magnetic beads, amplified by RD-PCR, and isolated from agarose gels to eliminate any contamination with full-length Control G/C. The fragments were sequenced using primers specific to the Control G/C PCR fragment. Sequencing chromatograms produced from these samples showed an abrupt end to the sequencing reaction 41 bases downstream from the mutation point, identical to the length of the linker, as would be expected if the end of the amplified fragment was encountered during sequencing. This result showed that indeed total elimination of full-length product results in removal of the secondary sequence from the chromatogram.

Figure 5A:
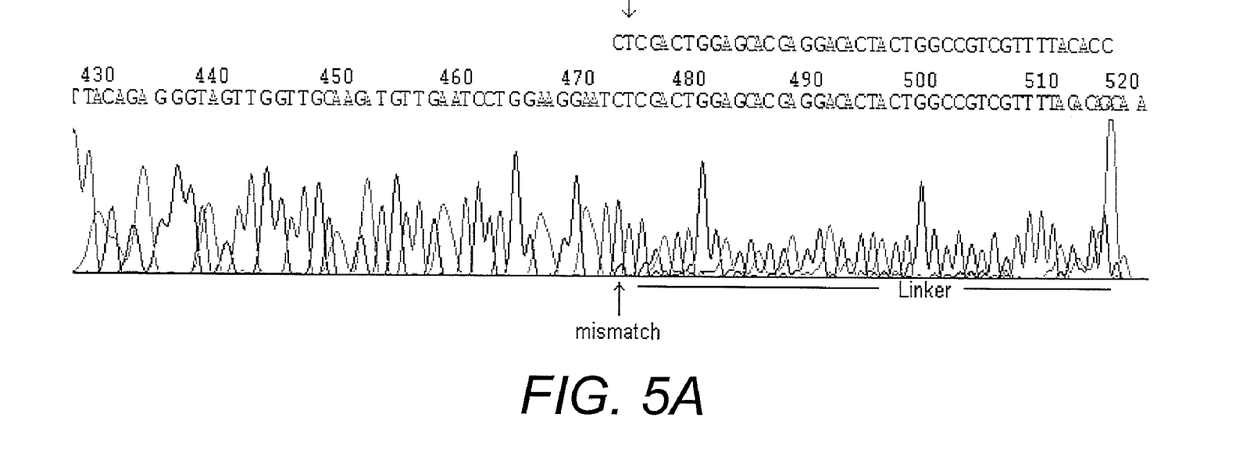
Figure 5B:
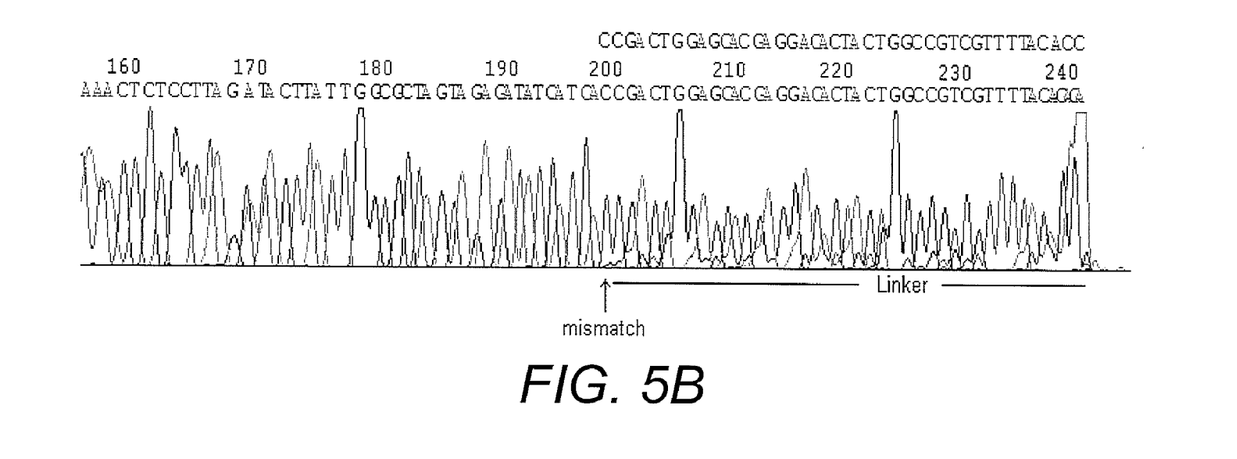

High MgCl$_2$ Concentrations Reduces SURVEYOR Nuclease 3'-to-5' Exonuclease Activity. SURVEYOR nuclease digestions for the experiments just described were carried out in the presence of 1.5 mM MgCl$_2$ and 10 mM MgCl$_2$. Sequencing chromatograms of agarose gel-purified RD-PCR products derived from Control G/C digested in 10 mM MgCl$_2$ showed clean sequences after the mutation point and the sequence of the linker was picked up by standard sequencing programs. A careful analysis of the chromatograms showed almost negligible contamination and very sharp peaks. A high Mg$^{2+}$ concentration suppresses the 3'-to-5' exonuclease activity of SURVEYOR nuclease sufficiently to produce amplified RD-PCR fragments that can be sequenced to yield readable chromatograms (FIGS. 5A and 5B).

SURVEYOR Nuclease Favors Digestion of C/C to G/G Mismatches in Control G/C. The sequencing chromatograms showed a mixture of C and G at the mutation point, as would be expected from SURVEYOR nuclease cleavage of the G/G and C/C containing heteroduplices in Control G/C. However, the peak corresponding to C was higher than the peak corresponding to G (FIGS. 5A and 5B). These results are consistent with previous data using mismatched oligonucleotides substrates to establish mismatch cutting preferences of SURVEYOR nuclease (Qiu, et al. (2004) supra) that indicated C/C is cut much more efficiently than G/G.

SURVEYOR Nuclease Produces an Asymmetric Cut at the Mismatch Site in Control G/C. When sequencing chromatograms from the RD-PCR fragment upstream of the mismatch site in Control G/C (450 bp) were compared with chromatograms from the fragment downstream of the mismatch (250 bp), an unexpected result was observed (FIGS. 5A and 5B). For the downstream 250-bp fragment, the sequence clearly showed that the 5'-end of the linker was ligated to the 3' G or C overhang at the mutation site. In contrast, a T was observed in the upstream 450-bp fragment between the 3'-end of the mutation and the 5'-end of the linker. In Control G/C DNA, there was a T adjacent and 3' to the mismatch C/G site. These results are consistent with SURVEYOR nuclease cutting the Control C/C heteroduplex 3' to the T adjacent and 3' to the C/C mismatch, producing a two-base CT 3'-overhang in one strand and a single base C 3'-overhang in the other strand.

Based upon the analysis conducted herein, particular embodiments of the present invention provide for the use of high concentrations of Mg$^{2+}$ (in the range of 1.5 to 20 mM) when employing SURVEYOR nuclease to efficiently capture the 3'-overhang at an endonuclease mismatch cut site.

What is claimed is:

1. A method for identifying the sequence of one or more variant nucleotides in a nucleic acid molecule comprising
   (a) contacting a double-stranded nucleic acid molecule with a mismatch-specific endonuclease, wherein one strand of said double-stranded nucleic acid molecule has one or more variant nucleotides which create at least one mismatch in the double-stranded nucleic acid molecule so that the double-stranded nucleic acid molecule is cleaved at the 3'-side of the mismatch by the mismatch-specific endonuclease;
   (b) ligating a double-stranded linker, containing a 3'-overhang, to the 3'-end of the strand with the one or more variant nucleotides, wherein the 3'-overhang of the linker is degenerate and the double-stranded portion of the linker is of a predetermined sequence; and
   (c) determining the sequence of the one or more variant nucleotides via the predetermined linker sequence thereby identifying the sequence of the one or more variant nucleotides.

2. The method of claim 1, wherein the 5'-end of at least one strand of the double-stranded nucleic acid molecule in step (a) is bound to a solid support.

3. The method of claim 1, wherein the 3'-ends of the double-stranded nucleic acid molecule in (a) are blocked.

4. The method of claim 1, wherein the strand with the one or more variant nucleotides is labeled.

5. The method of claim 1, wherein step (c) is carried out by sequencing-by-synthesis from the predetermined linker sequence.

6. The method of claim 1, wherein step (c) is carried out by
   (i) denaturing the double-stranded portion of the linker;
   (ii) hybridizing a complementary primer to the predetermined linker sequence in the presence of an intercalating fluorescence resonance energy transfer (FRET) donor;

(iii) contacting the product of step (ii) with DNA Polymerase and at least one ddNTP labeled with a FRET acceptor to extend the complementary primer; and (iv) detecting FRET, wherein the presence of FRET is indicative of the sequence of the variant nucleotide.

7. The method of claim 1, wherein the double-stranded linker is detectably labeled.

8. The method of claim 1, wherein the double-stranded nucleic acid molecule of step (a) is produced by a polymerase chain reaction.

9. The method of claim 8, wherein the polymerase chain reaction is carried out with a universal primer.

10. The method of claim 9, wherein the 5'-end of the universal primer is bound to a solid support.

11. A kit for identifying the sequence of one or more variants in a nucleic acid molecule comprising a mismatch-specific endonuclease that cleaves a double stranded nucleic acid molecule at the 3'-side of a mismatch; and a double-stranded linker, containing a 3'-overhang, wherein the 3'-overhang of the linker is degenerate and the double-stranded portion of the linker is of a predetermined sequence.

12. The kit of claim 11, further comprising a primer complementary to the predetermined sequence of the linker;

an intercalating FRET donor; and ddCTP, ddATP, ddTTP, and ddGTP each labeled with a different FRET acceptor.

* * * * *